United States Patent
Spector

(10) Patent No.: US 6,352,558 B1
(45) Date of Patent: *Mar. 5, 2002

(54) METHOD FOR PROMOTING REGENERATION OF SURFACE CARTILAGE IN A DAMAGE JOINT

(75) Inventor: Myron Spector, Brookline, MA (US)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,981

(22) Filed: Dec. 29, 1999

Related U.S. Application Data

(63) Continuation-in-part of application No. 08/894,517, filed as application No. PCT/GB96/00399 on Feb. 22, 1996.

(51) Int. Cl.⁷ .................................................. A61F 2/30
(52) U.S. Cl. ................ 623/18.11; 623/908; 623/23.76; 623/20.14
(58) Field of Search ........................... 623/16.11, 18.11, 623/20.14, 20.17, 23.63, 23.72, 917; 606/82, 84, 110, 184, 185, 186

(56) References Cited

U.S. PATENT DOCUMENTS

| | | | |
|---|---|---|---|
| 5,167,961 A | 12/1992 | Lussi et al. | |
| 5,417,975 A | 5/1995 | Lussi et al. | |
| 5,567,806 A | 10/1996 | Abdul-Malak | |
| 5,573,771 A | 11/1996 | Geistlich et al. | |
| 5,624,463 A * | 4/1997 | Stone et al. | 623/23.61 |
| 5,759,190 A | 6/1998 | Vibe-Hansen | |
| 5,837,278 A | 11/1998 | Geistlich et al. | |
| 6,221,109 B1 * | 4/2001 | Geistlich et al. | 623/17.11 |

FOREIGN PATENT DOCUMENTS

| | | |
|---|---|---|
| GB | 9518638 | 7/1995 |
| GB | 9625961 | 8/1996 |
| GB | 9802976 | 4/1999 |
| US | 9624310 | 8/1996 |

OTHER PUBLICATIONS

H.A. Breinan et al., "Reparative Tissues in Articular Cartilage Defects in a Canne Model Treated By Microfracture", 45th Annual Meeting, Orthopaedic Research Society, Feb. 1–4, 1999, Anaheim, CA.

C.R. Lee et al., "Harvest and Selected Repair Procedures Affect Mechanical and Biochemical Properties of Uninvolved Articular Cartilage in the Canine Knee", 45th Annual Meeting, Orthopaedic Research Society, Feb. 1–4, 1999, Anaheim, CA.

C.R. Lee et al., "The Contractile Behavior of Articular Chondrocytes in Collagen Matrices in Vitro", Tissue Engineering Soc., Orlando, Fla., Dec. 4–6, 1998.

S.M. Mueller et al., "Alpha–Smooth Muscle Actin in Bovine Meniscus Cells Seeded in Type I and Type II Collagen–Gag Matrices", 44th Annual Meeting, Orthopaedic Research Society, Mar. 16–19, 1998, New Orleans, Louisiana.

S. Nehrer et al., "Chrondrocyte–Seeded Type I and Type II Collagen Implants Investigated in Vitro", Fifth World Biomaterials Congress, May 29–Jun. 2, 1996, Toronto, CA.

(List continued on next page.)

Primary Examiner—Bruce Snow
Assistant Examiner—Brian E. Pellegrino
(74) Attorney, Agent, or Firm—Rothwell, Figg, Ernst & Manbeck

(57) ABSTRACT

A method of promoting regeneration of surface cartilage of a joint includes the steps of forming punctures in a subchondral plate of an area of the joint to be treated, covering the puncture and the area to be treated with a chondrocyte-free patch made of a sheet of collagen membrane material without adding chondrocytes to the area to be treated, fixing the patch over the area to be treated, and allowing the area to be treated to regenerate cartilage without adding chondrocytes to the area to be treated.

20 Claims, 4 Drawing Sheets

OTHER PUBLICATIONS

S. Nehrer et al., "Autologous Chondrocyte–Seeded Type I and II Collagen Matrices Implanted in a Chondral Defect in a Canine Model", 44th Annual Meeting, Orthopaedic Research Society, Mar. 16–19, 1998, New Orleans, Louisiana.

S. Nehrer et al., "Chondrocyte–Seeded Type I and Type II Collagen Matrices Implanted in a Chondral Defect in a Canine Model", 7th Conference European Orthopaedic Research Society, Barcelona, 1997.

S. Nehrer et al., "Characteristics of Articular Chondrocytes Seeded in Collagen Matrices in Vitro", Tissue Engineering, Vol. 4, No.2, 1998, pp. 175–183.

S. Nehrer et al., "Matrix Collagen Type and Pore Size Influence Behaviour of Seeded Canine Chondrocytes", Biomaterials 18, (1997), pp. 769–776.

Donna Schulz–Torres et al., "Tendon Cell Contraction of Collagen–Gag Matrices In Vitro: Effect of Cross–Linking", Soc. for Biomaterials, Providence, R.I., Apr. 28–May 2, 1999.

T.O. Schneider et al., "Expression of α–Smooth Muscle Actin in Canine Intervertebral Disc Cells in Situ and in Collagen–Gag Matrices In Vitro", J. Orthopaedic Research In press, pgs. 1–22.

S. Nehrer et al., "Canine Chondrocytes Seeded in Type I and Type II Collagen Implants Investigated In Vitro", Jan. 29, 1997, John Wiley & Sons, Inc., pp. 95–104.

S.M. Mueller et al., "α–Smooth Muscle Actin and Contractile Behavior of Bovine Meniscus Cells Seeded in Type I and Type II Collagen–Gag Matrices", Sep. 18, 1998, John Wiley & Sons, Inc., 1999, pp. 1–10.

Genzyme Tissue Repair, "Carticel$_{198}$ (autologous cultured chondrocytes), Engineering a Better Repair", Genzyme Tissue Repair, 64 Sidney Street, Cambridge, MA 02139–4136, 9/97, brochure.

* cited by examiner

METHOD FOR PROMOTING REGENERATION OF SURFACE CARTILAGE IN A DAMAGE JOINT

CROSS-REFERENCE TO RELATED APPLICATIONS

The present application is a continuation-in-part of U.S. Ser. No. 08/894,517, filed Nov. 10, 1997, which is a §371 of PCT/GB96/00399, filed Feb. 22, 1996, which claims priority from Great Britain Application No. 9503492.2, filed Feb. 22, 1995.

BACKGROUND OF THE INVENTION

1. Field of the Invention

The present invention relates to the field of promoting regeneration of surface cartilage in damaged joints.

2. Description of the Background Art

In view of the large number of joint injuries, such as knee injuries, which take place yearly, a number of therapies have been developed in an effort to promote regeneration of damaged cartilage. Typical methods involve introduction of chondrocytes from an outside source into the damaged area to promote cartilage regeneration.

For example, in accordance with one method, a cartilage biopsy is surgically removed from the patient and sent to a laboratory, where the patient's chondrocytes are isolated from the cartilage and the chondrocyte cells are reproduced in culture. Later, another surgery is performed on the patient wherein the damaged cartilage area to be treated is debrided back to expose healthy cartilage, leaving the subchondral bone plate intact. A periosteal patch is taken from the proximal medial tibia of the patient, and this periosteal patch is sutured to the rim of the healthy cartilage surrounding the area to be treated. The cultured chondrocytes reproduced from the cells previously taken from that patient then are injected under the patch into the defect, and the injury is allowed to heal.

U.S. Pat. No. 5,759,190 discloses another method, wherein a hemostatic barrier is placed proximal to the surface to be treated, chondrocytes in a matrix are placed upon the surface to be treated distal to the hemostatic barrier, and then the matrix is covered with a patch.

All of the above-described methods, in which the damaged area to be treated is covered with a patch, require multiple surgical procedures on the patient, wherein chondrocytes are removed from the patient, sent to a laboratory for culturing, and then the cultured chondrocytes are returned for implantation in to the patient in another surgical procedure.

There remains a need in the art for improved methods of promoting regeneration of surface cartilage in damaged joints so as to reduce the number of surgical procedures performed on a patient and eliminate the need for implanting cultured chondrocytes in the patient.

SUMMARY OF THE INVENTION

In accordance with the present invention, a method of promoting regeneration of surface cartilage of a joint includes the steps of forming a plurality of punctures in a subchondral plate of an area of the joint to be treated, covering the punctures and the area to be treated with a chondrocyte-free patch made of a sheet of collagen membrane material without adding chondrocytes to said area to be treated, fixing the patch over said area to be treated, and allowing said area to be treated to regenerate cartilage without adding chondrocytes to said area to be treated.

DETAILED DESCRIPTION OF THE INVENTION

The present invention provides a method for repairing injuries and damage to surface cartilage in joints such as knees. In accordance with one embodiment, cartilage defects are removed from the injured area to be treated, for example, by scraping of calcified cartilage from the injured area.

Figure 1:
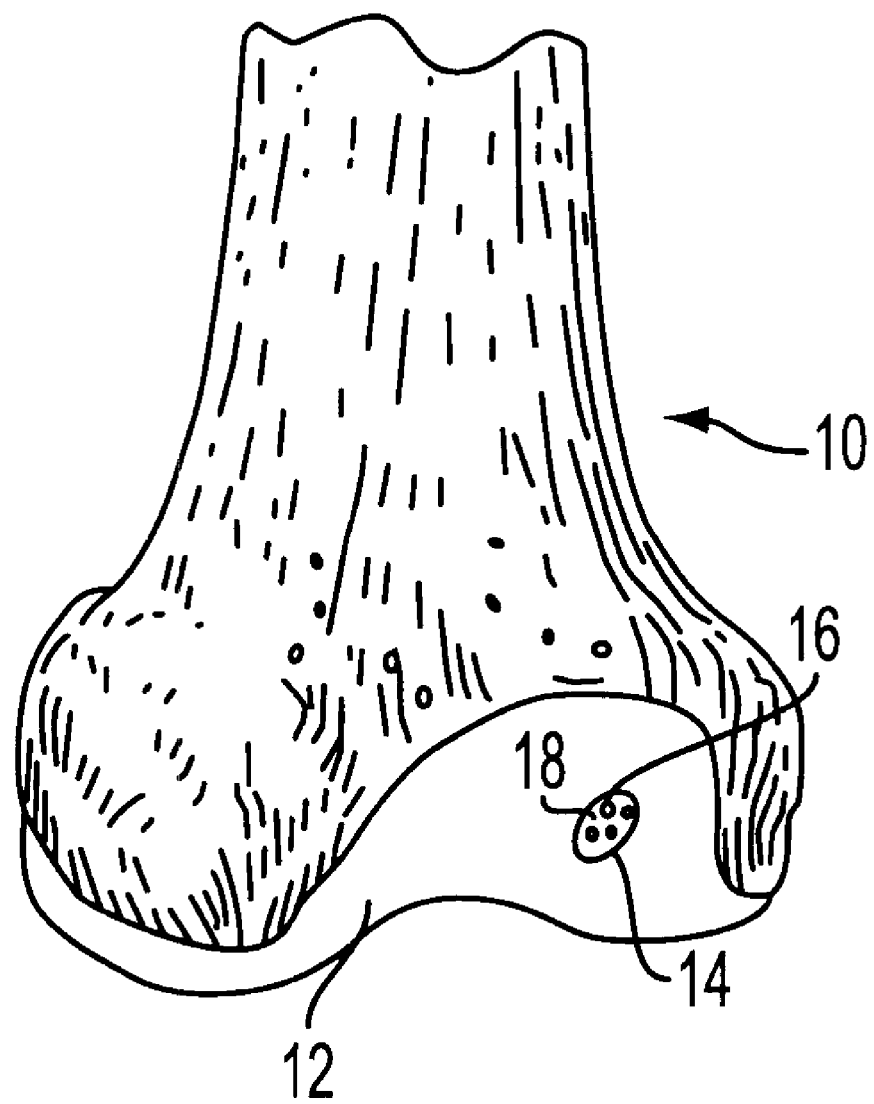
FIG. 1 is a perspective view with portions broken away showing an injured area of surface cartilage of a bone joint end member, with subchondral plate puncturing in accordance with the present invention.

After scraping of the calcified cartilage, a plurality of punctures are formed in the subchondral plate of the area of injury utilizing a microfracture technique. FIG. 1 shows a bone 10 with cartilage 12 showing an area of injury 14 to be treated, wherein calcified cartilage has been scraped from the area to be treated. A plurality of punctures 16 have been formed in the subchondral plate 18 of the area of injury.

The punctures 16 in the subchondral plate can be formed, for example, with a straight pointed end of a microsurgical pick to a depth of, e.g., about 0.5–5 mm, more preferably about 1.5–2 mm. The punctures 16 may have a width of, for example, about 0.2–1.5 mm, more preferably about 0.5–1 mm, and most preferably about 0.8 mm.

Although the invention has been described with respect to utilization of the above-described microfracture technique involving forming a plurality of punctures in the subchondral plate, it is believed that the invention also is applicable to other methods of puncturing the subchondral plate, such as drilling, abrasion and the like.

After forming the punctures in the subchondral plate as described above, the punctures in the area to be treated are covered by a patch 20 comprised of a chondrocyte-free sheet of collagen membrane material without adding any cultured chondrocytes to the area to be treated.

Figure 2:
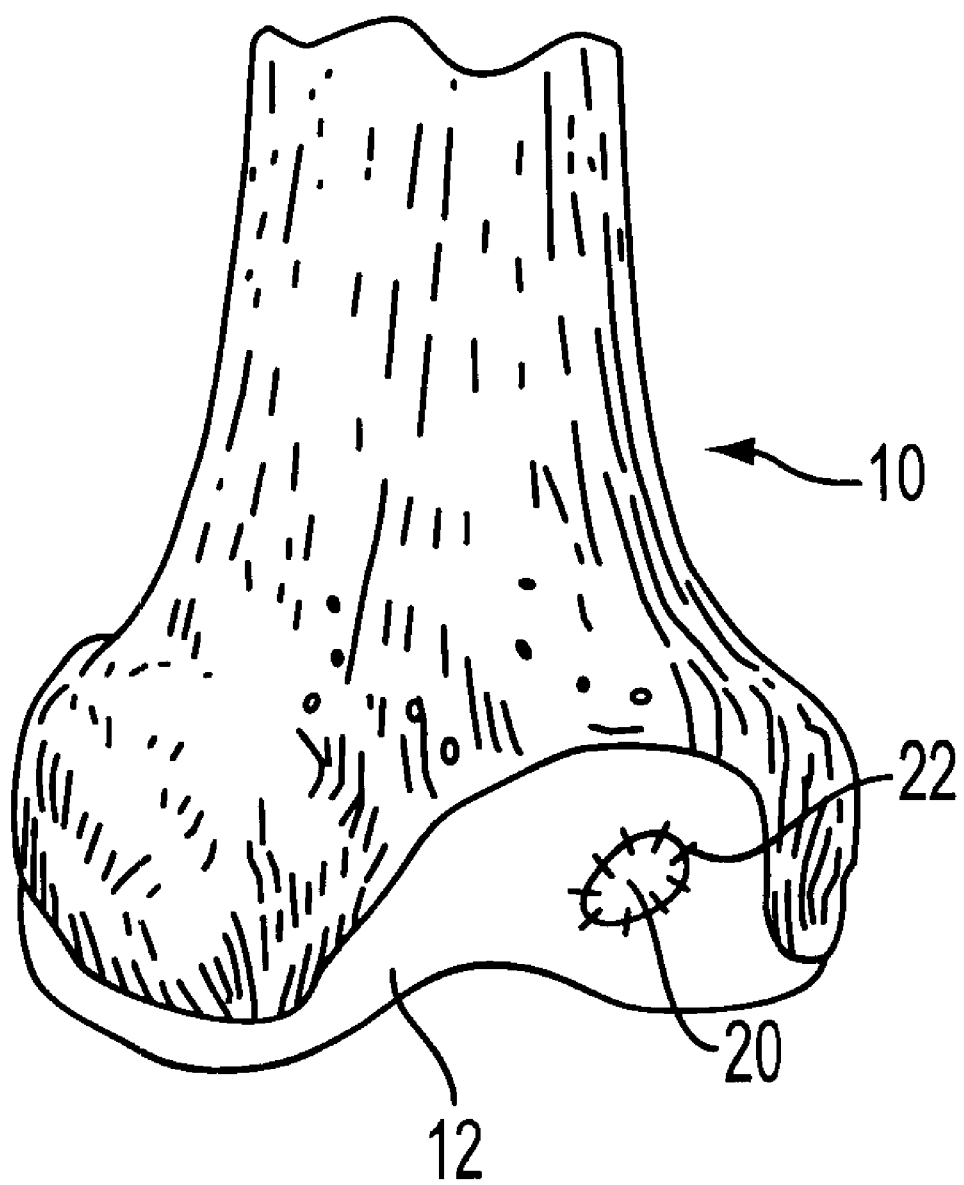
FIG. 2 is a perspective view with portions broken away showing the bone joint of FIG. 1 following covering the injured area with a chondrocyte-free patch made of a sheet of collagen membrane material in accordance with the present invention.

The patch then is fixed over the area to be treated, for example, by sutures 22 as shown in FIG. 2. Alternatively, the patch may be fixed over the area to be treated by adhesively bonding the patch to the cartilage surrounding the area to be treated, for example, utilizing an organic glue as is known in the art, or any other suitable method.

The patched area then is allowed to regenerate cartilage without adding cultured chondrocytes to the area to be treated at any time during the healing process.

In accordance with one embodiment, the sheet of collagen membrane material which is utilized for a patch is formed predominantly of collagen II. One suitable collagen II material suitable for use in accordance with the present invention is described in U.S. Ser. No. 08/894,517, filed Nov. 10, 1997, incorporated herein by reference.

In accordance with another embodiment, the collagen membrane material is comprised of at least one barrier layer having at least one smooth face 116 so as to inhibit cell adhesion thereon and act as a barrier to prevent passage of cells therethrough. See FIG. 3. In accordance with this embodiment, the barrier layer further has a fibrous face 118 opposite the smooth face 116, the fibrous face allowing cell growth thereon. The smooth face 116 preferably is oriented away from the area to be treated, and the fibrous face 118 preferably is oriented toward the area to be treated. In preferred embodiments, the barrier layer is predominantly collagen I, collagen III or a mixture thereof. One suitable material is Biogide®, from Ed. Geistlich Söhne AG für Chemische Industrie, the assignee of the present invention. The Biogide® material is described in U.S. Pat. No. 5,837,278, incorporated herein by reference.

Figure 3:
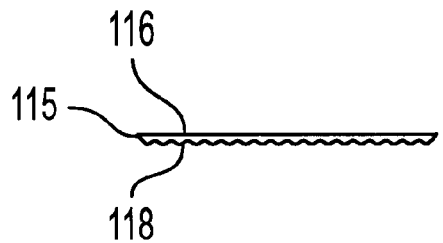
FIG. 3 is a side elevation schematic view showing a single-layered membrane for use in accordance with the present invention.
Figure 4:
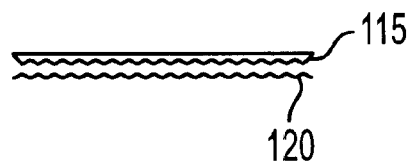
FIG. 4 is a side elevation schematic view showing a double-layer membrane for use in accordance with the present invention.

FIG. 4 shows still another type of membrane which may be used in accordance with the present invention. This membrane includes a barrier layer 115 as shown in FIG. 3, and further includes a matrix layer 120 predominantly of collagen II having an open sponge-like texture. A collagen membrane as shown in FIG. 4 is described in PCT application no. PCT/GB98/02976, and U.S. Ser. No. 09/545,465, filed Apr. 7, 2000, claiming priority from U.K. patent application no. 9721585.9, filed Oct. 10, 1997, incorporated herein by reference.

In yet another embodiment, a collagen membrane material as shown in FIG. 4 is utilized, wherein the barrier layer 115, the matrix layer 120, or both are impregnated with a glycosaminoglycan. Examples of suitable glycosaminoglycans include hyaluronic acid, chondroitin 6-sulphate, keratin sulphate or dermatan sulphate.

Figure 5:
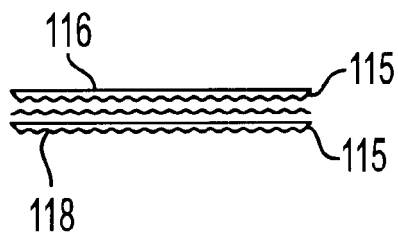
FIG. 5 is a side elevation schematic view showing a triple-layer membrane for use in accordance with the present invention.

FIG. 5 shows still another type of membrane suitable for use in accordance with the present invention. The membrane of FIG. 5 includes two barrier layers 115, between which is sandwiched a resorbable polymer layer. In preferred embodiments, the polymer is a polylactic acid polymer.

Figure 6:
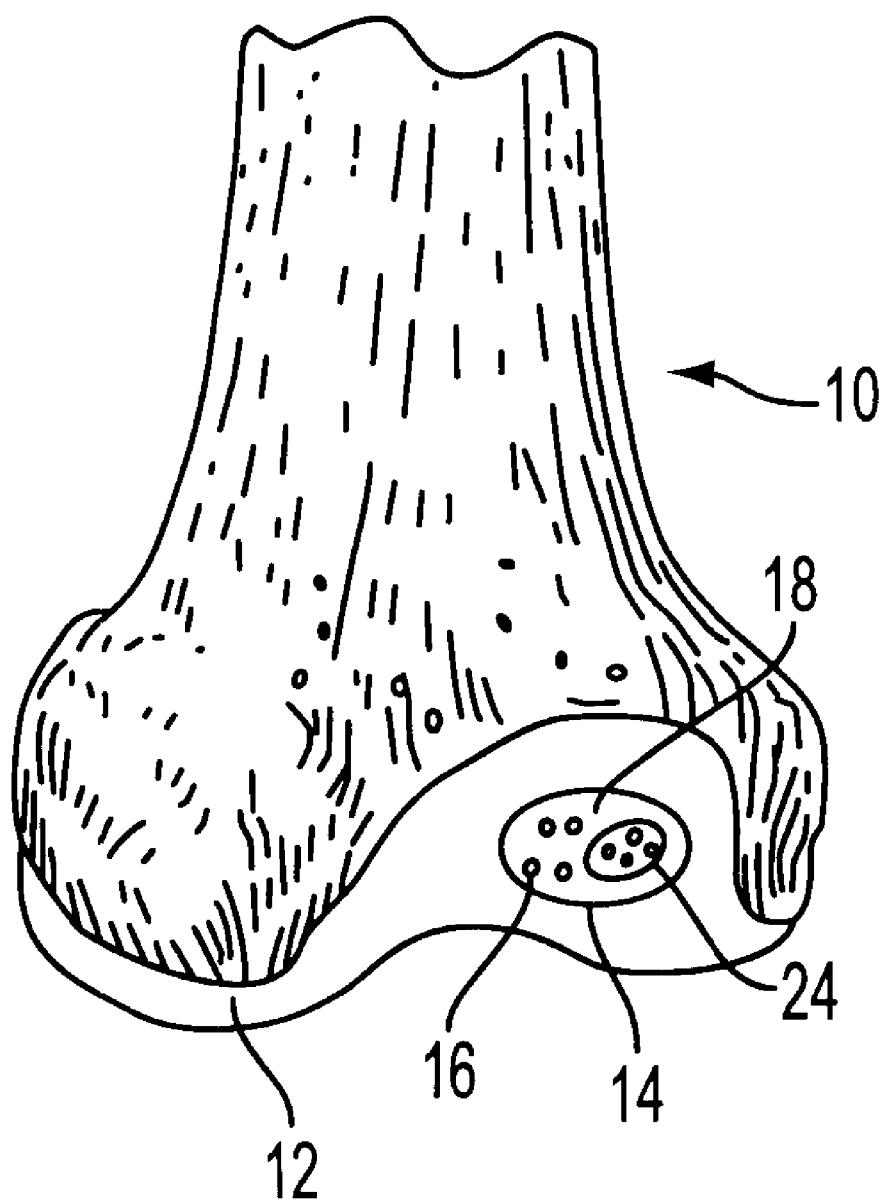
FIG. 6 is a perspective view of the bone joint end member with portions broken away, showing subchondral puncturing and a bone mineral implant in accordance with another embodiment of the present invention.

In accordance with another embodiment, involving more substantial injuries which include injuries to the underlying bone as well as to the surrounding surface cartilage of a joint, an implant material 24 such as resorbable bone mineral may be implanted into the bone injury within the area to be treated. See FIG. 6. Punctures 16 may be made in the subchondral plate area 18 to be treated, and thereafter, a collagen membrane patch can be fixed over the area to be treated as shown in FIG. 2.

One suitable implant material is Bio-Oss® from Ed. Geistlich Söhne AG Für Chemische Industrie, the assignee of the present invention. Bio-Oss® is described in U.S. Pat. Nos. 5,167,961 and 5,417,975, incorporated herein by reference. Another suitable implant material is Bio-Oss Collagen® from Ed. Geistlich Söhne AG Für Chemische Industrie, which is resorbable bone mineral in a collagen matrix. Bio-Oss Collagen® is described in U.S. Pat. No. 5,573,771, incorporated herein by reference.

Since many modifications, variations and changes in detail may be made to the described embodiments, it is intended that all matter in the foregoing description and shown in the accompanying drawings be interpreted as illustrative and not in a limiting sense.

What is claimed is:

1. A method of promoting regeneration of surface cartilage of a joint, comprising:

forming a plurality of punctures in a subchondral plate of an area of said joint to be treated;

covering the area to be treated, including the plurality of said punctures, with a chondrocyte-free patch comprised of a sheet of collagen membrane material without adding chondrocytes to said area to be treated;

fixing the patch over said area; and allowing said area to regenerate cartilage without adding chondrocytes to said area.

2. The method of claim 1 further including the step of removing cartilage defects from said area to be treated, prior to forming said punctures.

3. The method of claim 2 wherein the step of removing said cartilage defects comprises scraping of calcified cartilage from said area to be treated.

4. The method of claim 1 wherein said punctures are formed to a depth of about 0.5–5 mm.

5. The method of claim 4 wherein said punctures have a width of about 0.2–1.5 mm.

6. The method of claim 5 wherein said punctures are formed to a depth of about 1.5–2 mm.

7. The method of claim 6 wherein said punctures have a width of about 0.5–1 mm.

8. The method of claim 7 wherein said punctures have a width of about 0.8 mm.

9. The method of claim 1 wherein said collagen membrane material is predominantly collagen II.

10. The method of claim 1 wherein said collagen membrane material is comprised of at least one barrier layer having at least one smooth face so as to inhibit cell adhesion thereon and act as a barrier to prevent passage of cells therethrough.

11. The method of claim 10 wherein said barrier layer further has a fibrous face opposite said smooth face, said fibrous face allowing cell growth thereon.

12. The method of claim 11 wherein said barrier layer is predominantly collagen I, collagen III or a mixture thereof.

13. The method of claim 10 wherein said collagen membrane further comprises a matrix layer predominantly of collagen II having an open sponge-like texture.

14. The method of claim 13 wherein said barrier layer, said matrix layer or both, are impregnated with glycosaminoglycan.

15. The method of claim 14 wherein the glycosaminoglycan is hyaluronic acid, chondroitin 6-sulphate, keratin sulphate or dermatan sulphate.

16. The method of claim 11 wherein said membrane material further comprises a second barrier layer, with a resorbable polymer layer sandwiched between the barrier layers.

17. The method of claim 16 wherein said polymer is a polylactic acid polymer.

18. The method of claim 1 wherein the patch is fixed over the area to be treated by adhesively bonding the patch to cartilage surrounding said area to be treated.

19. The method of claim 1 wherein the patch is fixed over the area to be treated by suturing the patch to cartilage surrounding said area to be treated.

20. The method of claim 1 further comprising implanting a chondrocyte-free resorbable bone mineral implant material into a region of bone injury in the area to be treated, prior to fixing said patch over said area to be treated.

* * * * *

UNITED STATES PATENT AND TRADEMARK OFFICE
Certificate

Patent No. 6,352,558                                                                                Patented: March 5, 2002

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Myron Spector, Brookline, MA; Peter Geistlich, Stansstad, Switzerland; and Lothar Schloesser, Darmstadt, Germany.

Signed and Sealed this Thirteenth Day of August, 2002.

<div style="text-align:right">

CORRINE M. MCDERMOTT
*Supervisory Patent Examiner*
Art Unit 3738

</div>